June 25, 1957 E. S. BOERNER Plant Pat. 1,611
ROSE PLANT
Filed Nov. 1, 1956
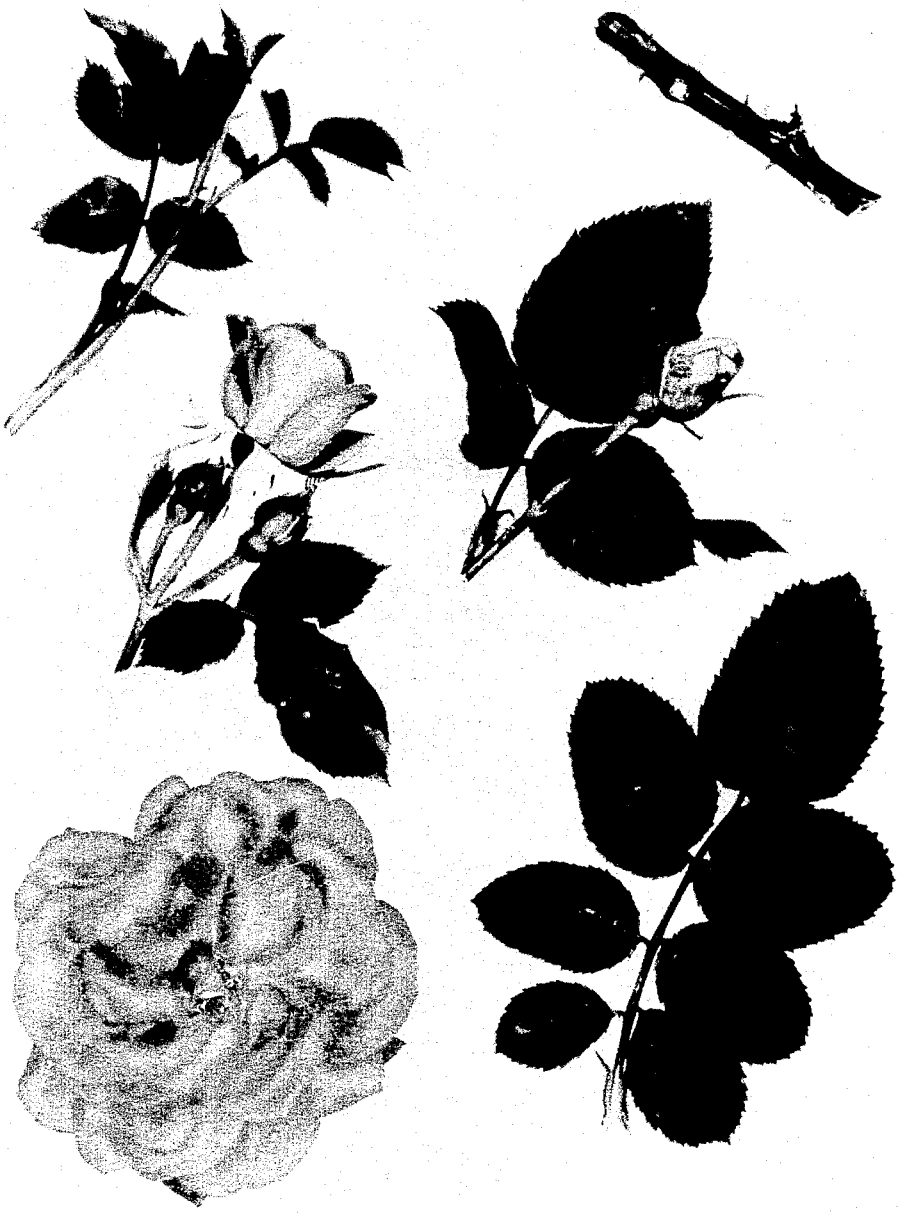
INVENTOR
E. S. Boerner
BY Robb and Robb
ATTORNEYS United States Patent Office Plant Pat. 1,611
Patented June 25, 1957

1,611

ROSE PLANT

Eugene S. Boerner, Newark, N. Y., assignor, by mesne assignments, to C. W. Stuart & Co., Newark, N. Y., a corporation of New York Application November 1, 1956, Serial No. 619,911

1 Claim. (Cl. 47—61)

The present invention relates to a new and distinct variety of rose plant of the hybrid polyantha class, which was originated by me by crossing the variety "Red Pinocchio" (Plant Patent No. 812) with the variety "Garnette" (unpatented).

As the result of this breeding, I have produced a new rose variety which is particularly characterized as to novelty by the following unique combination of outstanding features:

(1) Bright green foliage which is particularly outstanding in the growing fields as compared with other varieties;

(2) A good Red Rose general color tonality of the flowers and the absence of fading of the flower color; and (3) Bright yellow stamens which show on the fully open flowers, giving the blooms life and sparkle.

The foregoing characteristics definitely differentiate my new variety from its parents, as well as from all other varieties of its class of which I am aware.

Asexual reproduction of the new variety by budding as performed at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart issued by the British Color Council in collaboration with the Royal Horticultural Society, except where general color terms of ordinary dictionary significance are obvious:

Type: Hardy; dwarf.
Class: Hybrid polyantha.
Breeding: Seedling.
*Seed parent.*—"Red Pinocchio."
*Pollen parent.*—"Garnette."
Propagation: Holds its distinguishing characteristics through succeeding propagations by budding.

*Flower*

Locality where grown and observed: Newark, New York.
Flowers borne: Several to stem; in irregular clusters; on stems of medium length and normal strength.
Quantity of bloom: Abundant, outdoors.
Continuity: Continuous.
Fragrance: Moderate.
Bud:
*Peduncle.*—Long; heavy; erect; smooth; with numerous yellow prickles. Color—light green.
*Before calyx breaks.*—Size—Medium. Form—ovoid; with a conspicuous neck; without foliaceous appendages on the surface of the bud; with entire foliaceous parts extending beyond the tip of the bud equal to ¼ or more of its length. Color—Pea Green, Plate 61/1.
*As calyx breaks.*—Color—Purple Madder, Plate 1028.
*As first petal opens.*—Size—medium. Form—ovoid. Color: outside—Chrysanthemum Crimson, Plate 824; inside—Cardinal Red, Plate 822.
*Opening.*—Opens up well.
Bloom:
*Size (when fully open).*—Medium; from 2¼ to 3 inches.
*Petalage.*—Double (more petals, but stamens not hidden); from 40 to 45 petals.
*Form.*—Flat-cupped, but becoming open-cupped; petals being at first loosely cupped, but later becoming loosely rolled outward at maturity.
Petals:
*Texture.*—Soft. Inside—velvety. Outside—satiny.
*Shape.*—Outside—obovate; lanceolate; with one notch. Intermediate—ovate; lanceolate; with one notch. Inside—obovate; lanceolate; with one notch.

This description of a newly opened flower was made from a rose grown in a greenhouse, in the month of May, at Newark, New York.

*Color.*—Outer petal: outside surface—Sulferino Purple, Plate 26; inside surface—Currant Red, Plate 821/1. Intermediate petal: outside surface—Solferino Purple, Plate 26/1; inside surface—Rose Red, Plate 724. Inner petal: outside surface—Tyrian Rose, Plate 24/1; inside surface—Rose Red, Plate 724.

This description was made from a rose that was open for 5 days in a greenhouse, in the month of May, at Newark, New York.

*Color.*—Outer petal: outside surface—Rose Bengal, Plate 25; inside surface—Currant Red, Plate 821/1. Inner petal: outside surface—Tyrian Purple, Plate 727/3; inside surface——Rose Red, Plate 724/1.
*General color effect.*—Newly opened flower—Rose Red, Plate 724. 3-days open—Rose Bengal, Plate 25.
*Behavior.*—Drop off cleanly.
*Flower longevity.*—Cut roses grown in greenhouse and kept at living room temperatures—6 days in May.

*Reproductive organs*

Stamens: Many; arranged regularly about pistils.
Filaments: Long; most with anthers. Color—Buttercup Yellow, Plate 5/3, flushed with Rose Madder, Plate 23/3.
Anthers: All open at once. Color—Buttercup Yellow, plate 5/3.
Pollen: Abundant. Color—gold.
Pistils: Many.
Styles: Uneven; medium length; heavy; loosely separated.
Stigma: Color—white.
Ovaries: All enclosed in calyx.
Hips: None.
Seeds: None.

*Plant*

Foliage:
*Leaves.*—Compound of 3 to 5 leaflets; abundant; medium size; moderately heavy.
*Leaflets.*—Shape—oval, with apex mucronate. Base—obtuse. Margin—doubly serrate.
*Color.*—Mature: upper surface—Parsley Green, Plate 00962; under surface—Lavender Green, Plate 000761. Young: upper surface—Scheele's Green, Plate 860; under surface—Lavender Green, Plate 000761/1.

*Rachis (the supporting stem of the compound leaf)*.—Medium caliper. Upper side—smooth. Under side—smooth.

*Stipules*.—Long; with medium points turning out at an angle of more than 45°.

*Disease resistance*.—Resistant to mildew and black-spot, as determined by comparison with other varieties grown under comparable cultural conditions at Newark, New York.

Growth:

*Habit*.—Bushy.

*Growth*.—Moderately vigorous.

*Canes*.—Medium heaviness.

*Main stems*.—Color—bright green. Thorns—several; medium length; straight; with long, narrow base. Prickles—none. Hairs—none.

*Branches*.—Color—bright green. Thorns—several; medium length; hooked downward; with long, narrow base. Prickles—none. Hairs—none.

*New shoots*.—Color—bright green. Thorns—several; medium length; with long, narrow base. Prickles—none. Hairs—none.

I claim:

A new and distinct variety of rose plant of the hybrid polyantha class, substantially as herein shown and described, characterized particularly as to novelty by its bright green foliage which is outstanding in the growing field in comparison with other varieties, the good Rose Red general color tonality of its flowers and the absence of fading of the flower color, and the bright yellow stamens which show on the fully open flowers and give the flowers life and sparkle.

No references cited.